US010912477B1

(12) United States Patent
Soleyman et al.

(10) Patent No.: US 10,912,477 B1
(45) Date of Patent: Feb. 9, 2021

(54) MODULAR CABLE ORGANIZATION SYSTEM

(71) Applicant: Pragmatic Medical Devices, LLC, Flower Mound, TX (US)

(72) Inventors: Emil Soleyman, Flower Mound, TX (US); Paul Simon, San Jose, CA (US); Craig Marion, Livermore, CA (US); Tina Asher Marion, Livermore, CA (US)

(73) Assignee: Pragmatic Medical Devices, LLC, Flower Mound, TX (US)

( * ) Notice: Subject to any disclaimer, the term of this patent is extended or adjusted under 35 U.S.C. 154(b) by 236 days.

(21) Appl. No.: 16/279,223

(22) Filed: Feb. 19, 2019

(51) Int. Cl.
| *H01B 7/00* | (2006.01) |
| *A61B 5/0428* | (2006.01) |
| *H02G 3/32* | (2006.01) |

(52) U.S. Cl.
CPC ....... *A61B 5/04286* (2013.01); *H01B 7/0045* (2013.01); *H02G 3/32* (2013.01)

(58) Field of Classification Search
CPC ..... A61B 5/04286; H01B 7/0045; H02G 3/32
See application file for complete search history.

(56) References Cited

U.S. PATENT DOCUMENTS

| 6,325,665 B1* | 12/2001 | Chung | H01R 13/72 439/501 |
| 9,800,031 B2* | 10/2017 | Irons | H02G 3/0616 |
| 2006/0286861 A1* | 12/2006 | Avevor | A61B 5/04286 439/501 |

* cited by examiner

Primary Examiner — Pete T Lee
(74) Attorney, Agent, or Firm — James E. Walton

(57) ABSTRACT

An assembly for supporting and retracting machine cables, thereby protecting operational components attached to machine cables. A cable organization system includes at least one modular cable management module fixed to a mounting plate that allows mounting of the cable organization system to a machine or other surface. The system has clamps which secure machine cables. The clamps are supported on top of pivoting guide tubes. The cable management modules contain retraction systems which retract the machine cable clamps from an extended position. By utilizing retracting cable clamps on pivoting guide tubes, the system allows the use of operational components attached to secured machine cables, and organizes the machine cables, so that the machine cables do not extend out into the floor around the machine. The system redirects pulling force on the machine cables, so that operational components do not get pulled onto the floor if a passerby catches on a machine cable.

20 Claims, 16 Drawing Sheets

MODULAR CABLE ORGANIZATION SYSTEM

BACKGROUND

1. Field of the Invention

The present invention relates generally to improvements in systems for retaining and organizing cables, and more specifically to systems for retaining and organizing cables on expensive medical equipment.

2. Description of Related Art

Modern medical equipment utilizes highly sophisticated machinery and components. Often medical equipment will include expensive and fragile probes or equipment attached to electrical cables which connect the equipment to a primary machine. For example, an ultrasound machine may utilize multiple probes on the end of cables, and often times these probes are secured in simple cups or brackets into which the expensive probes fit. While such a method may secure the probes, there still exists a risk that the probes will be damaged.

While medical equipment may be secured to a machine when not in use, often times the cables that attach the equipment to the machine are not stored or organized in any particular way and, instead, simply lie on the floor. Therefore there is a risk that persons or other equipment may snag or pull on the electrical cables. If the force on the cables is great enough, attached medical equipment, such as probes, may be pulled from whatever means are being used to secure the probes, resulting in damage to the probes. This risk is far greater when the concerned machine is actually being used.

Often times, when equipment, such as an ultrasound machine, is being used, the probes may be temporarily placed on a nearby flat surface or on top of the machine. Because the machine is in use and people are present and moving about the area, there is a high risk that a person will accidentally snag a cable and pull a probe onto the floor. Because the probes are fragile, they easily break upon falling to the floor. A single probe typically costs several thousand dollars. Therefore, a machine with unorganized or loose cables can very easily be a monetary risk.

Modern medical machines usually have several cables attached to them. The more cables a machine has, and the longer the cables, the greater the financial risk created by inadequately secured or organized cables. Therefore there exists a need for a simple and efficient means by which equipment cables may be secured and organized, thereby preventing expensive damage to equipment.

BRIEF DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
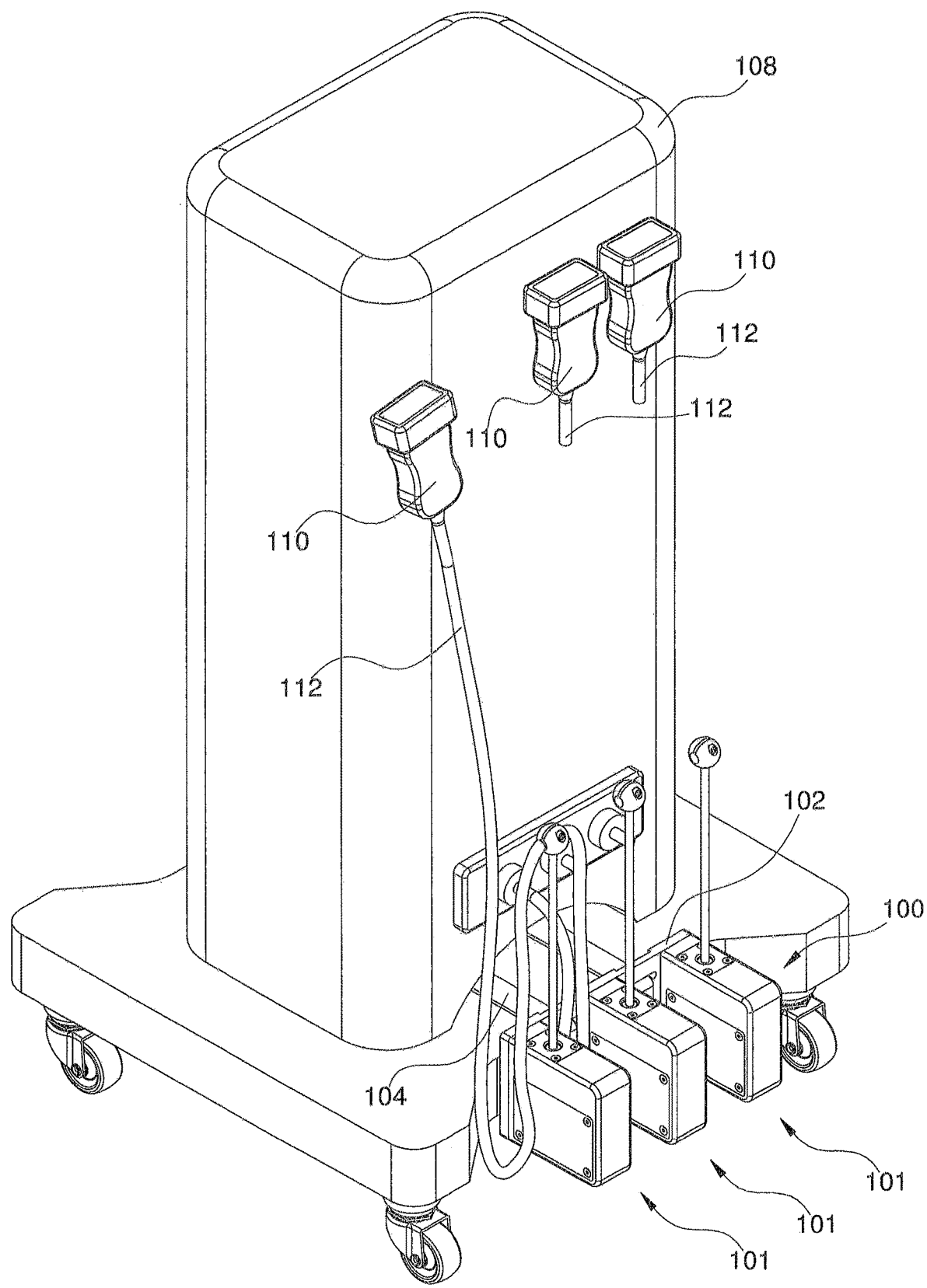
FIG. 1 is a perspective view of a cable organization system according to the preferred embodiment of the present application attached to an ultrasound machine.

While the assembly and method of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the cable organizational system according to the present application are provided below. It will of course be appreciated that in the development of any actual embodiment, numerous implementation-specific decisions will be made to achieve the developer's specific goals, such as compliance with assembly-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Referring now to FIG. 1 in the drawings, a cable organization system 100 is shown attached to an ultrasound machine 108. Cable organization system 100 is generally comprised of at least one cable management module 101 attached to a mounting plate 102. As shown in FIG. 1, mounting plate 102 is secured to the base of ultrasound machine 108 with mounting member 104. Mounting member 104 is preferably one or more straps that fit through strap apertures 106 (see FIG. 7) formed in mounting plate 102; however, it will be appreciated that mounting member 104 may be any suitable mechanism for securing mounting plate 102 to ultrasound machine 108, such as clamps, clips, hooks, magnets, adhesive, hook and loop tape, etc. Ultrasound machine 108 includes one or more probes 110 attached to the machine with cables 112. For clarity, portions of certain cables 112 are not shown.

Figure 2:
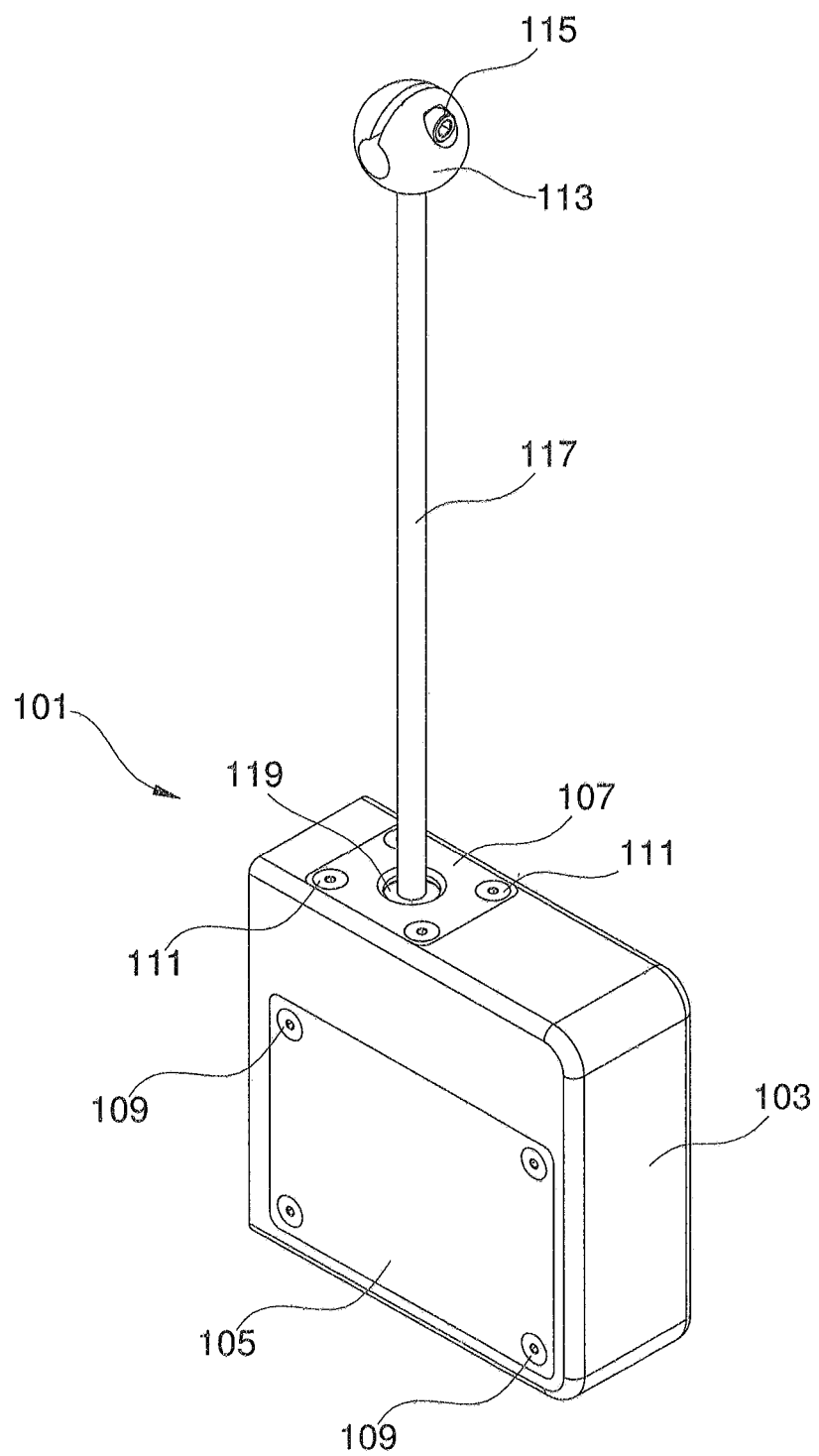
FIG. 2 is a perspective view of a cable management module according to a preferred embodiment of the present application.
Figure 3:
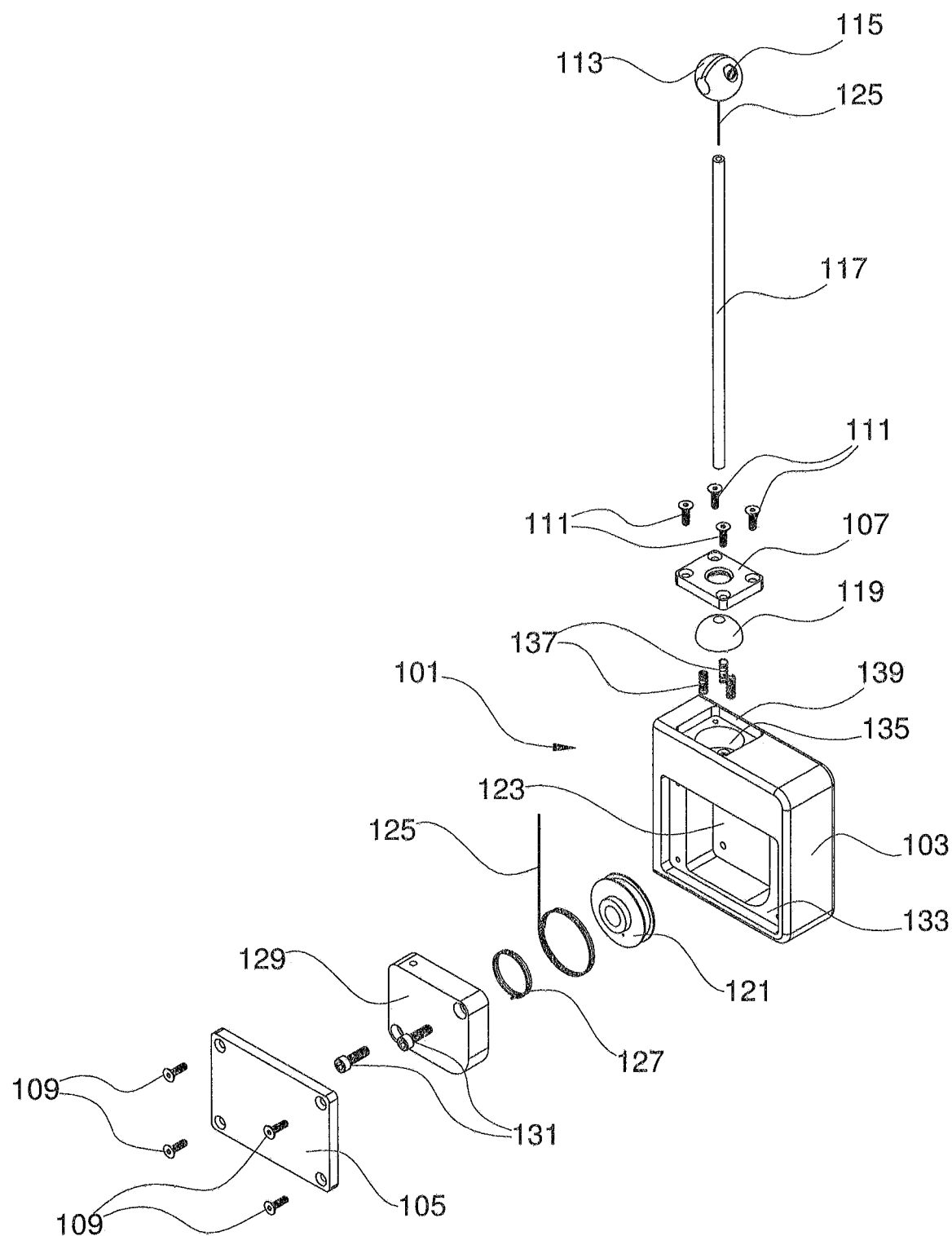
FIG. 3 is an exploded view of the cable management module of FIG. 2.

Referring now also to FIGS. 2 and 3 in the drawings, cable management module 101 is depicted. Module 101 generally comprises a main housing 103, a main housing cover plate 105, a pivot cover plate 107, a cable clamp 113, a guide tube 117, and a pivot 119. As shown in FIG. 2, main cover plate 105 is attached to main housing 103 by bolts 109, and pivot cover plate 107 is attached to main housing 103 by bolts 111. It should be understood though that cover plates 105 and 107 may be attached to main housing 103 by a variety of means, such as screws, magnets, tabs, clips, friction, bolts, and/or adhesive.

Main housing 103 contains a spool 121 which operates within spool opening 123. Spool opening 123 is a recessed area within main housing 103. A retractor cable 125 is operably wrapped around spool 121. It should be understood that retractor cable 125 passes through main housing 103 and through guide tube 117 to ultimately be attached to cable clamp 113. A torsion spring 127 places tension on spool 121 to provide a winding force to spool 121. Spool 121, retractor cable 125, and torsion spring 127 are contained within retractor housing 129. Retractor housing 129 fits into spool opening 123 and is preferably secured by bolts 131. The interior portion of main housing 103 containing spool opening 123 and retractor housing 129 is covered by main housing cover plate 105, which fits into main cover plate opening 133.

Although main housing cover plate 105, pivot cover plate 107, retractor housing 129, spool opening 123, main cover plate opening 133, and pivot cover plate opening 139 have been shown as having generally rectangular shapes, it should be understood though that components may have a variety of shapes. For example, spool opening 123 may have a generally circular shape, as might pivot cover plate 107, and pivot cover plate opening 139. Other features or openings may be of any suitable shape depending on design choices and physical limitations.

In operation, torsion spring 127 places tension on spool 121 to wind in retractor cable 125. In this way, cable clamp 113 is held in place in a retracted position at an upper end of guide tube 117. Cable clamp 113 utilizes a clamp tensioner 115 to provide a clamping force to a cable held within cable clamp 113. As is shown, cable clamp 113 may be a spherical clamp, preferably made of a durable and flexible material, such as rubber, plastic, and/or nylon, and has a channel cut through one side of cable clamp 113. The channel may have different widths along its depth and may terminate at a hole that is sized and shaped to accommodate cable 112. Clamp tensioner 115, shown in FIGS. 2 and 3 as a bolt or set screw, extends through a transverse hole in clamp 113 and through the channel formed in clamp 113. In operation, to secure cable 112 in cable clamp 113, clamp tensioner 115 is removed from cable clamp 113, and cable 112 is pressed into the channel in clamp 113. Clamp tensioner 115 is then placed into clamp 113 and adjusted, so that cable 112 is secured within the hole through cable clamp 113.

Although cable clamp 113 has been shown as a generally spherical ball having a channel of different widths and tensioner 115, it will be appreciated that cable clamp 113 may be in the form of a variety of different shapes and configurations. For example, the channel may be of a uniform width and may hold cable 112 in a press-fit fashion. In other embodiments, cable clamp may have hinged components that open and close in a pivoting fashion to secure cable 112. A wide variety of configurations may be utilized, provided the cable 112 is releasably and securely held in place relative to cable clamp 113.

It should be understood that cable clamp 113 and cable tensioner 115 represent one embodiment of a cable clamp design, and cable management module 101 or alternative embodiments of a cable organization system 100 may use any appropriate design of a cable clamp. In some embodiments, like in the preferred embodiment, a cable clamp may use distinct clamps and tensioners, whereas other embodiments may use cable clamps which include a tensioning mechanism as part of the clamp design. Other embodiments may use various forms of clamps and tensioners, such as hook-and-loop type straps, elastic straps or clamps, clamps secured by hinged latches, or clamps with springs. In addition, clamp tensioner 115, though shown as a bolt, should be understood for purposes of the preferred embodiment to include any tensioner that would effectively work with clamp 113 as disclosed. For example, tensioner 115 may be a hinged latch across the channel that opens to allow a cable to be inserted.

Cable clamp 113 is held at one end of guide tube 117 when in a retracted position. To allow greater freedom of movement for cables held in clamp 113, guide tube 117 pivots at varying angles with respect to multiple axes (see FIG. 8). Guide tube 117 is attached to pivot 119. Pivot 119 is preferably a multi-axis pivot, i.e., a hemispherical pivot. Pivot 119 fits into pivot seat 135, which is a recess formed in main housing 103. Pivot 119 is secured into pivot seat 135 by pivot cover plate 107, which fits into pivot cover plate opening 139 formed in main housing 103 above pivot seat 135. The range of motion of guide tube 117 is limited by the opening formed in pivot cover plate 107 through which guide tube 117 passes.

Figure 4:
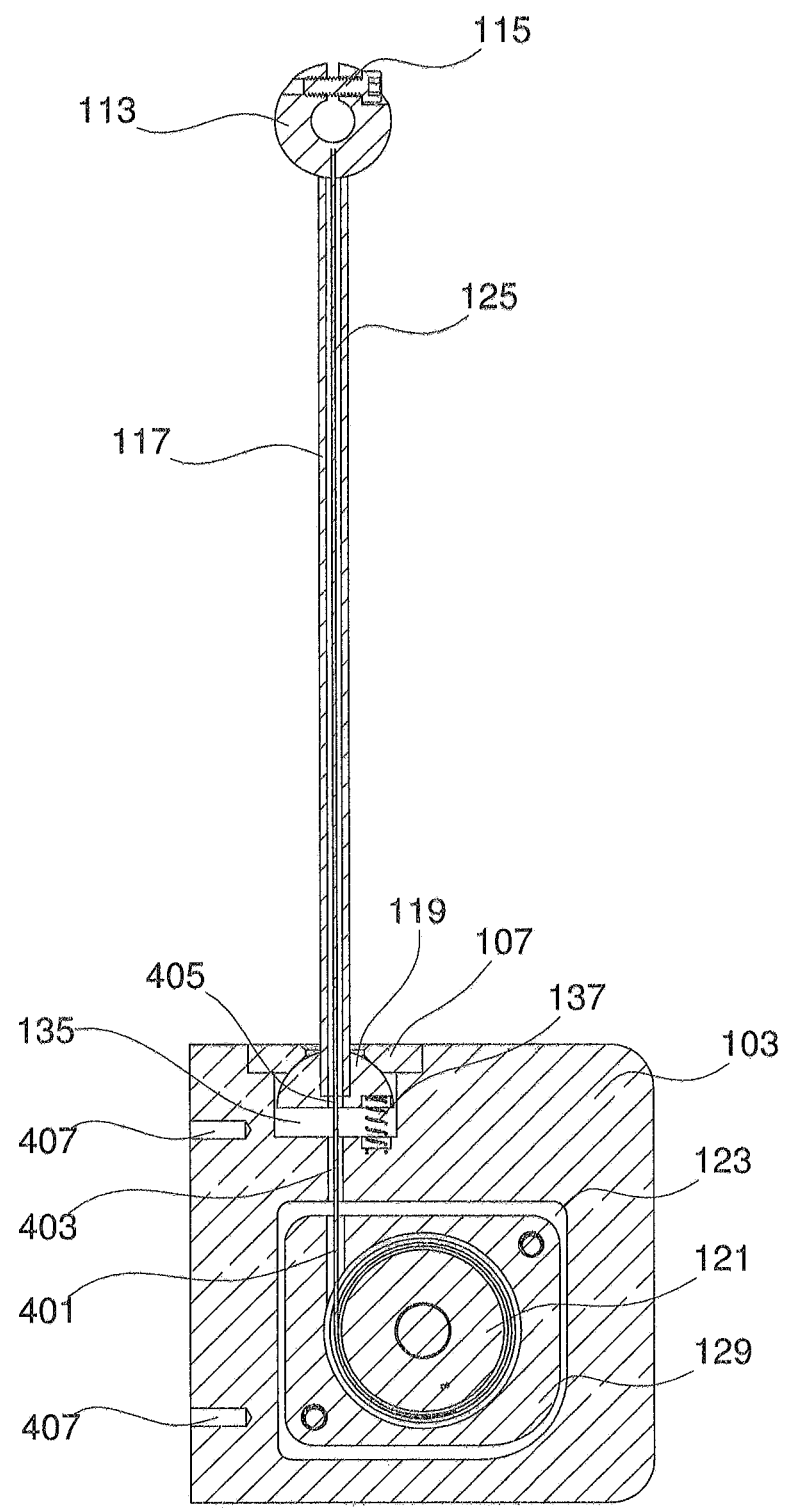
FIG. 4 is a cross-sectional view of the cable management module of FIG. 2, taken along a vertical plane.

Referring now also to FIG. 4 in the drawings, tension is provided to pivot 119 by at least one pivot tensioner 137 in order to bring pivot 119 and guide tube 117 into an upright equilibrium position when cable clamp 113 is in a retracted position. Multiple pivot tensioners 137, for example compression coil springs, may be used between pivot 119 and pivot seat 135. For clarity, only one such spring is shown in FIG. 4. However, pivot tensioner 137 should be understood to include any elastic compression components held between pivot 119 and pivot seat 135. For example, in an alternative embodiment, an elastomeric material may be used to provide tension to a pivot mechanism. Alternative embodiments of a cable management module may utilize pivots similar to the multi-axis pivot found in the preferred embodiment, or may use single-axis pivots (see FIGS. 10-12). Alternative pivot designs may use a variety of means to return guide tubes 117 to an upright and/or equilibrium position, such as wound springs, torsion springs, compression coil springs, tension coil springs, elastic bands, or elastic sponges.

As shown in FIG. 4, cable management module 101 is configured to operate to retract cables held in clamp 113. Retractor cable 125 is shown wrapped around spool 121, which is contained within spool opening 123 by retractor housing 129. Retractor housing 129 includes a retractor housing cable aperture 401 formed therein having sufficient clearance for cable 125 to pass through retractor housing 129. Retractor cable 125 also passes through a main housing cable aperture 403 which is formed through an interior portion of main housing 103 opening into pivot seat 135. Pivot 119 has a pivot cable aperture 405 formed through it to allow retractor cable 125 to pass into guide tube 117.

Guide tube 117 is shown to be a hollow tube through which retractor cable 125 passes until retractor cable 125 arrives at and is attached to cable clamp 113. Main housing 103 further has mounting apertures 407 for mounting module 101 directly to equipment or to mounting plates, which are then fixed to equipment or other surfaces.

In the preferred embodiment, retractor cable 125 is permanently attached to cable clamp 113. However, it should be understood that cable 125 may also be removably attached to cable clamp 113. For example, retractor cable 125 may have a screw feature permanently attached at a clamp end of cable 125, and that screw feature may be used to removably attach cable 125 to cable clamp 113, or cable 125 may be simply tied to cable clamp 113.

Certain components of cable management module 101, such as main housing 103, cover plates 105 and 107, and retractor housing 129 are preferably made of durable and cost-efficient materials such as polymers, aluminum, and/or stainless steel. Guide tube 117 is preferably a rigid guide tube made of material such as polymer, aluminum, and/or stainless steel. In alternative embodiments, guide tube 117 may instead be a flexible guide tube made of tough flexible materials, such as flexible plastics, nylons, and/or rubbers. Certain operational components, such as springs or pivots, may be made of whatever material satisfies the functional requirements of those components. Retractor cable 125 is preferably a durable fabric or synthetic cord, such as a braided nylon cord. Alternative embodiments of a cable management module 101 may utilize higher-strength retractor cables, such as small-diameter braided-steel cable.

Figure 5:
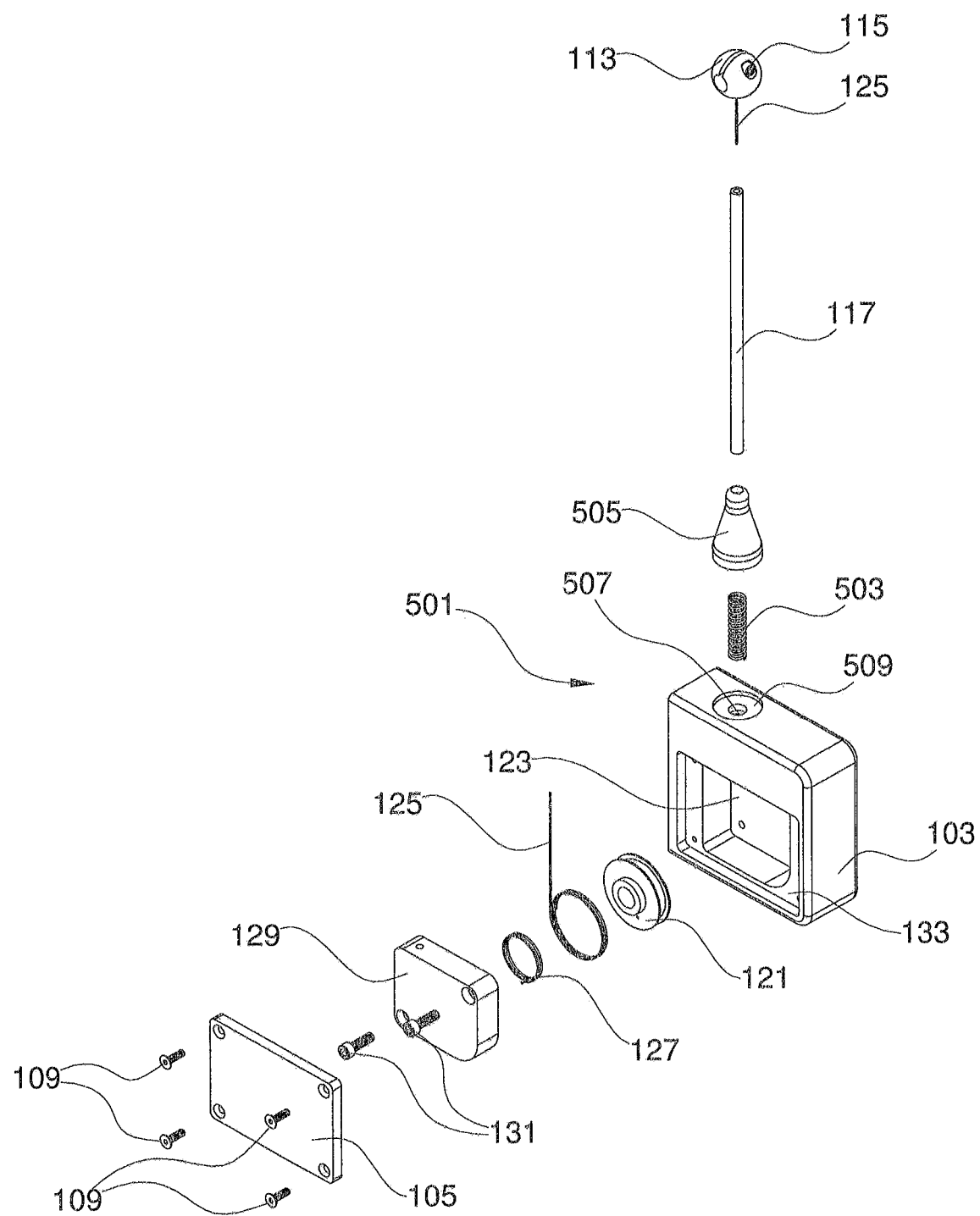
FIG. 5 is an exploded view of an alternate embodiment of a cable management module according to the present application.
Figure 6:
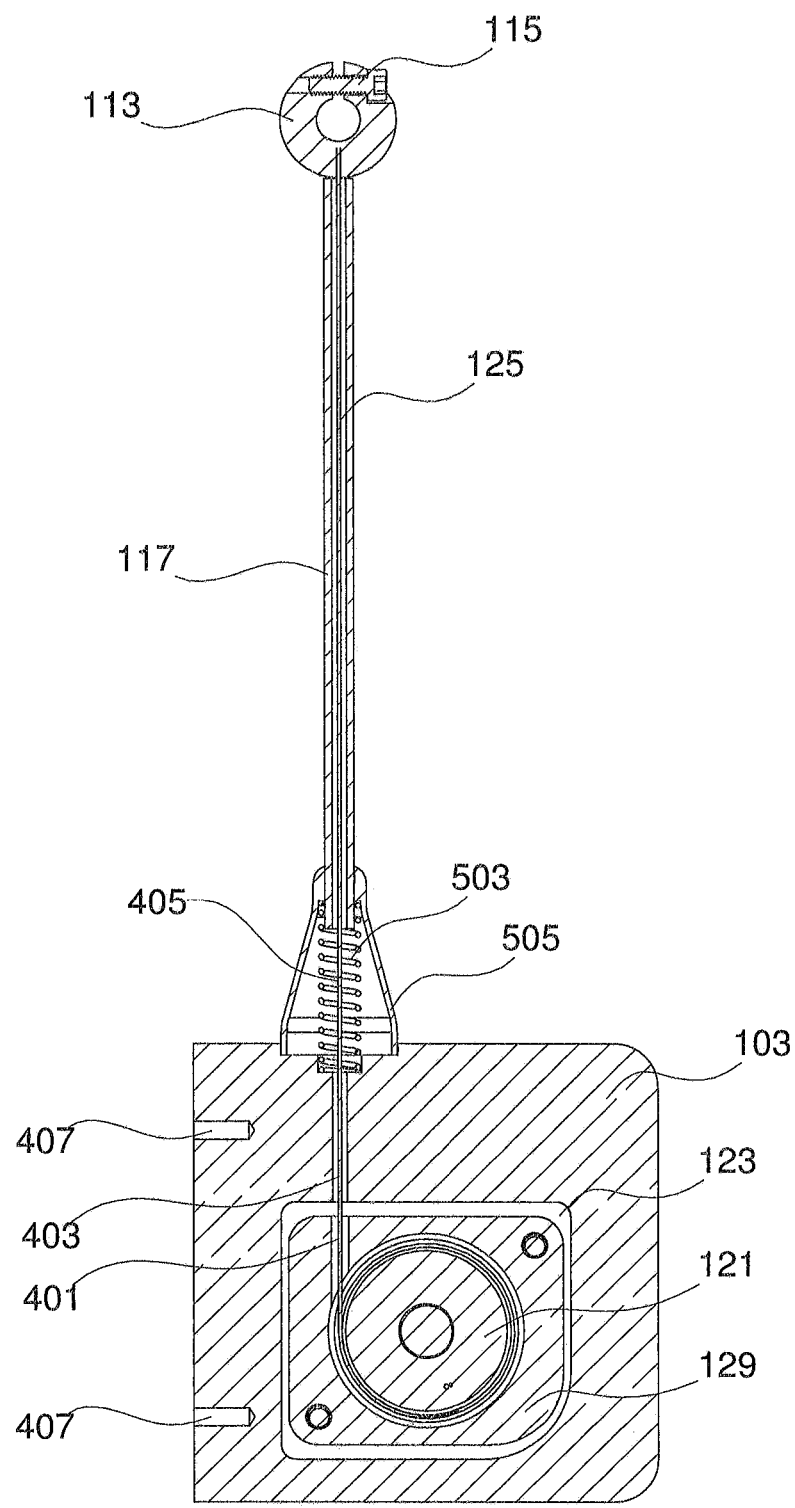
FIG. 6 is a cross-sectional view the cable management module according to FIG. 5 taken along a vertical plane.

Referring now also to FIGS. 5 and 6 in the drawings, an alternative embodiment of cable management module 501 is shown. Module 501 is substantially similar in form and function to module 101, other than the pivoting mechanism used. Cable management module 501 utilizes the same main housing 103, main housing cover plate 105, cable clamp 113, guide tube 117, retractor cable 125, and other spooling and retraction internals as module 101. However, module 501 does not contain a pivot 119, pivot cover plate 107, bolts 111, pivot tensioner 137, pivot seat 135, or pivot cover plate opening 139. Instead, in module 501, guide tube 117 fits into bending spring 503. Guide tube 117 should be understood to partially extend longitudinally into bending spring 503, but not all the way into or through bending spring 503.

Housing 103, as part of module 501, has a spring seat 507 instead of a pivot seat 135, and has a flexible cover seat 509 instead of pivot cover plate opening 139. Bending spring 503 mounts into and is secured by spring seat 507, and is covered by a flexible cover 505 that fits into and is secured by flexible cover seat 509 (see FIG. 6). Retractor cable 125 extends longitudinally through bending spring 503 and further through guide tube 117 into cable clamp 113. As a coil spring mounted into spring seat 507, bending spring 503 performs similarly to pivot 119 in that it functions as a multi-axis pivot. Furthermore, as a spring, bending spring 503 does not need an additional pivot tensioner as pivot 119 does.

Figure 7:
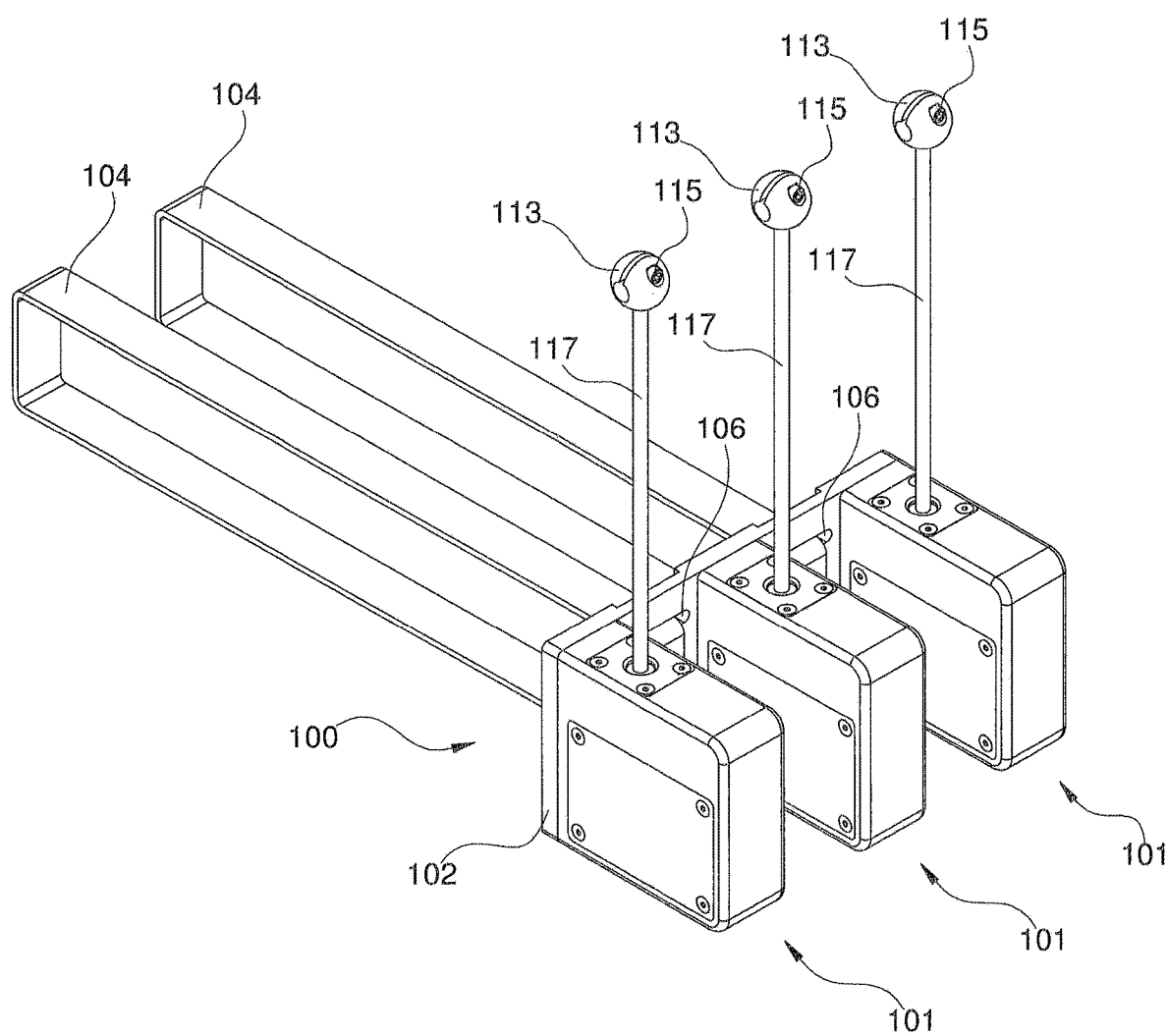
FIGS. 7 and 8 are perspective views of a cable organization system according to a preferred embodiment of the present application.
Figure 8:
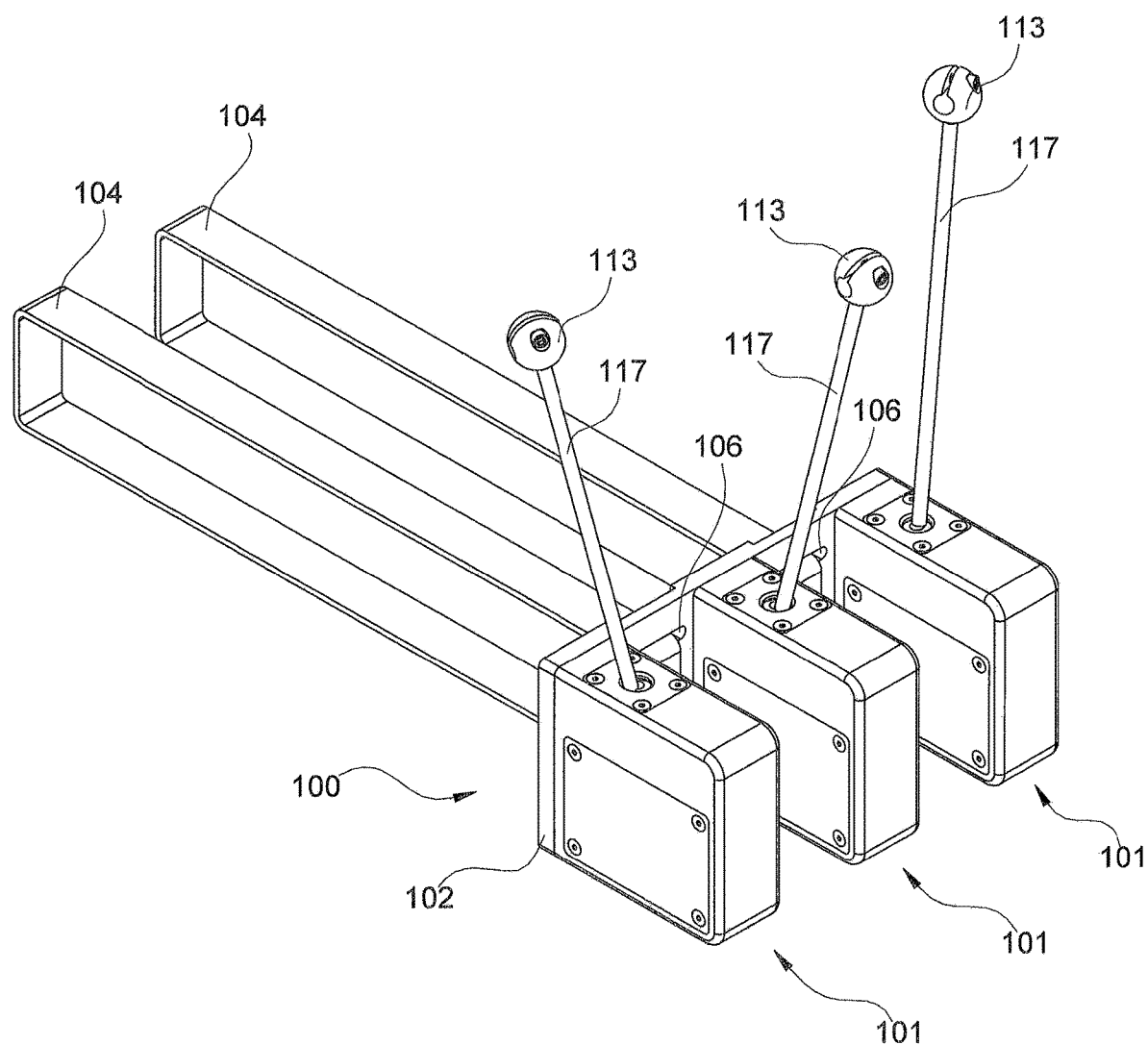

Referring now also to FIGS. 7 and 8 in the drawings, cable organization system 100 is shown. Cable organization system 100 comprises multiple cable management modules 101 attached to a mounting plate 102. Each module 101 is preferably attached to mounting plate 102 with bolts that fit into mounting apertures 407 formed in main housing 103 (see FIG. 4). In alternative embodiments, cable management modules 101 may be attached to mounting plate 102 by a variety of means, such as screws, bolts, clips, or adhesive, and modules 101 may be removably attached to mounting plate 102 or may be permanently fixed to mounting plate 102. According to the preferred embodiment, which uses bolts that fit into mounting apertures 407 in main housing 103, cable management modules 101 are removably attached to mounting plate 102.

In the embodiment of FIGS. 7 and 8, mounting plate 102 is configured to support three cable management modules 101. However, it should be understood that, because cable organization system 100 is modular, mounting plate 102 may be sized and configured to support only one cable management module 101, or may be sized and configured to support any plurality of cable management modules 101 or other cable management modules. For example, a user may prefer a cable organization system 100 that supports five equipment cables, therefore requiring a mounting plate 102 that supports five modules, such as module 101. Alternative embodiments of a cable organization system 100 may utilize alternative embodiments of cable management modules 101. For example, mounting plate 102 could readily be used with the cable management module 501 described above, or with any other module embodiment with a main housing footprint similar to the footprint of main housing 103. As shown in FIGS. 7 and 8, cable management modules 101 are spaced apart on mounting plate 102. However, it should be understood that in the preferred embodiment or in an alternative embodiment, cable management modules 101 may be coupled together to form one unit with multiple pivoting guide tubes.

Cable organization system 100 preferably mounts to a machine or piece of equipment with straps 104. Straps 104 fit through strap apertures 106 formed in mounting plate 102. Straps 104 are preferably made of a durable and inexpensive material, such as nylon webbing. Straps 104 preferably are adjustable so that cable organization system 100 may be properly tightened onto a machine or piece of equipment. Each strap 104 preferably forms a loop when cable organization system 100 is mounted to a piece of machinery or equipment. Straps 104 may be secured and adjusted with a variety of means. For example, straps 104 may be tightened with adjustable buckles, or with ratcheting mechanisms such as those found on commonly available ratchet straps.

Cable organization system 100 is depicted as having two straps 104 configured to pass over and under the base of ultrasound machine 108. It should be understood though that cable organization system 100 may utilize any appropriate number of straps depending on the size of mounting plate 102, the number of cable management modules 101 supported by mounting plate 102, and the weight of the equipment cables held in cable clamps 113. For example, a system that supports only two modules 101 may be effective with only one strap 104, while a system that supports seven modules 101 might require three straps 104. In addition, straps 104 may be configured to pass around the sides of ultrasound machine 108.

Alternative embodiments of a cable organization system may use other mounting plate designs to support mounting the system to surfaces such as beds, walls, or poles. For example, a mounting plate may have apertures formed through it such that a cable organization system similar to system 100 could be screwed directly to a wall or bedside. Alternatively, a mounting system may use brackets or clamps to attach a mounting plate to a pole such as an IV fluids stand.

Figure 9:
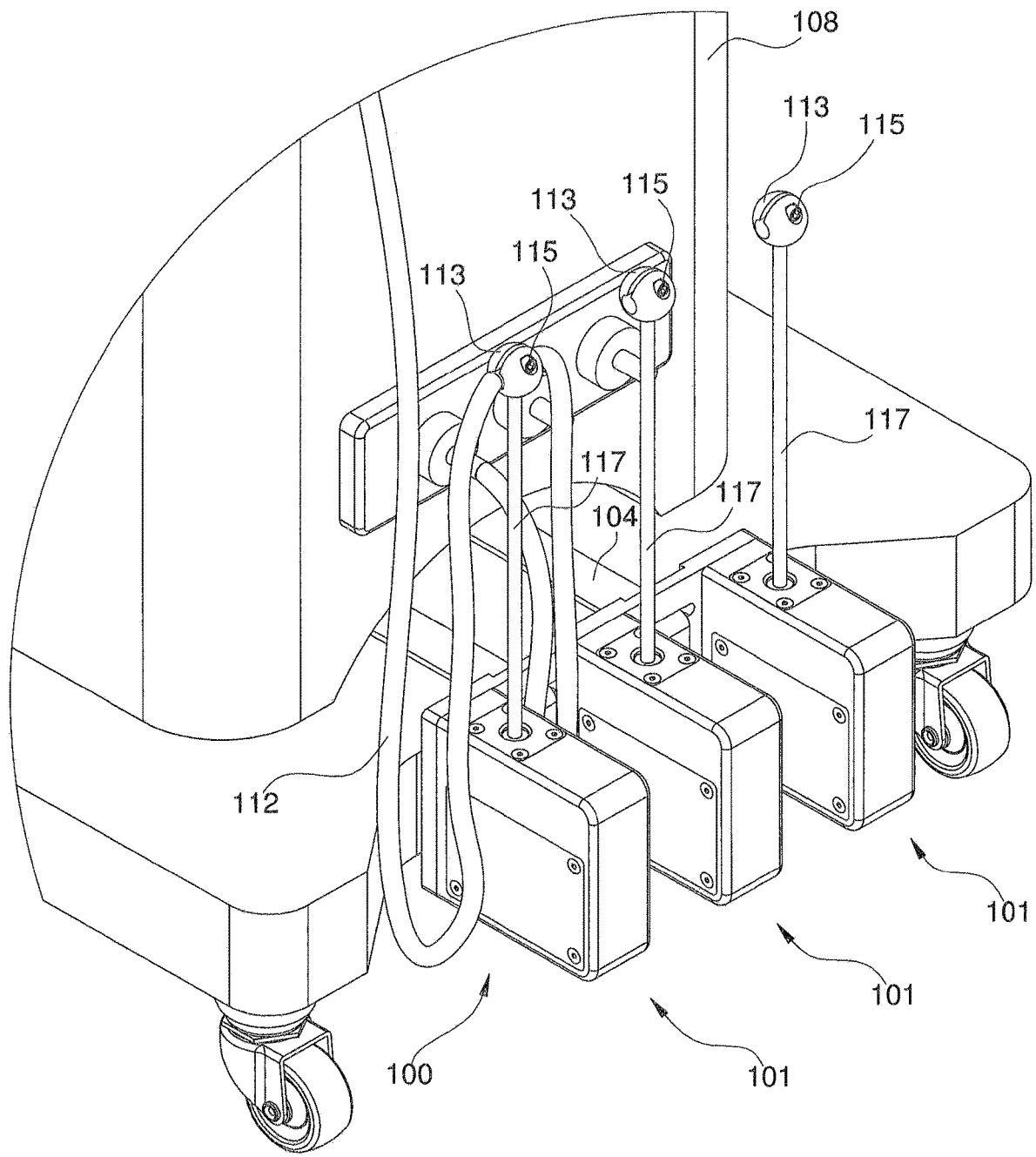
FIG. 9 is an enlarged view of the cable organization system of FIG. 1.

Referring now also to FIG. 9 in the drawings, cable organization system 100 is shown in use on a piece of medical equipment, specifically an ultrasound machine 108.

Ultrasound machine 108 has multiple probes 110 attached to ultrasound machine 108 by cables 112. For clarity, portions of certain cables 112 are not shown. Straps 104 wrap around the base of ultrasound machine 108 and secure cable organization system 100 to the machine. In use, a cable 112 is secured into a cable clamp 113 at a selected point along the length of cable 112. Each cable 112 is preferably mounted into a cable clamp 113, such that only the minimum length of a cable 112 needed to allow full use of a probe 110 is present between cable clamp 113 and probe 110. The remaining portion of cable 112 is held between cable clamp 113 and ultrasound machine 100.

Because cable clamps 113 are mounted at the top of upright guide tubes 117, cables 112 are supported and preferably do not have portions lying out in the floor area adjacent ultrasound machine 108, such that a passing person or piece of equipment can catch one of the cables 112. Furthermore, because only the minimal length of cable 112 necessary for full use of probes 110 is present between cable clamps 113 and probes 110, any portions of a cable 112 that may be exposed on the floor to moving persons or equipment would likely be the portion of a cable 112 held between a cable clamp 113 and ultrasound machine 801. The effect of this is that, if a passing person or piece of equipment does catch a cable 112, the pulling force on cable 112 will be directed into a respective cable management module 101. This prevents probes 110 from being pulled off the machine or out of their mounts when a passing person or piece of equipment catches on a cable 112.

Figure 10:
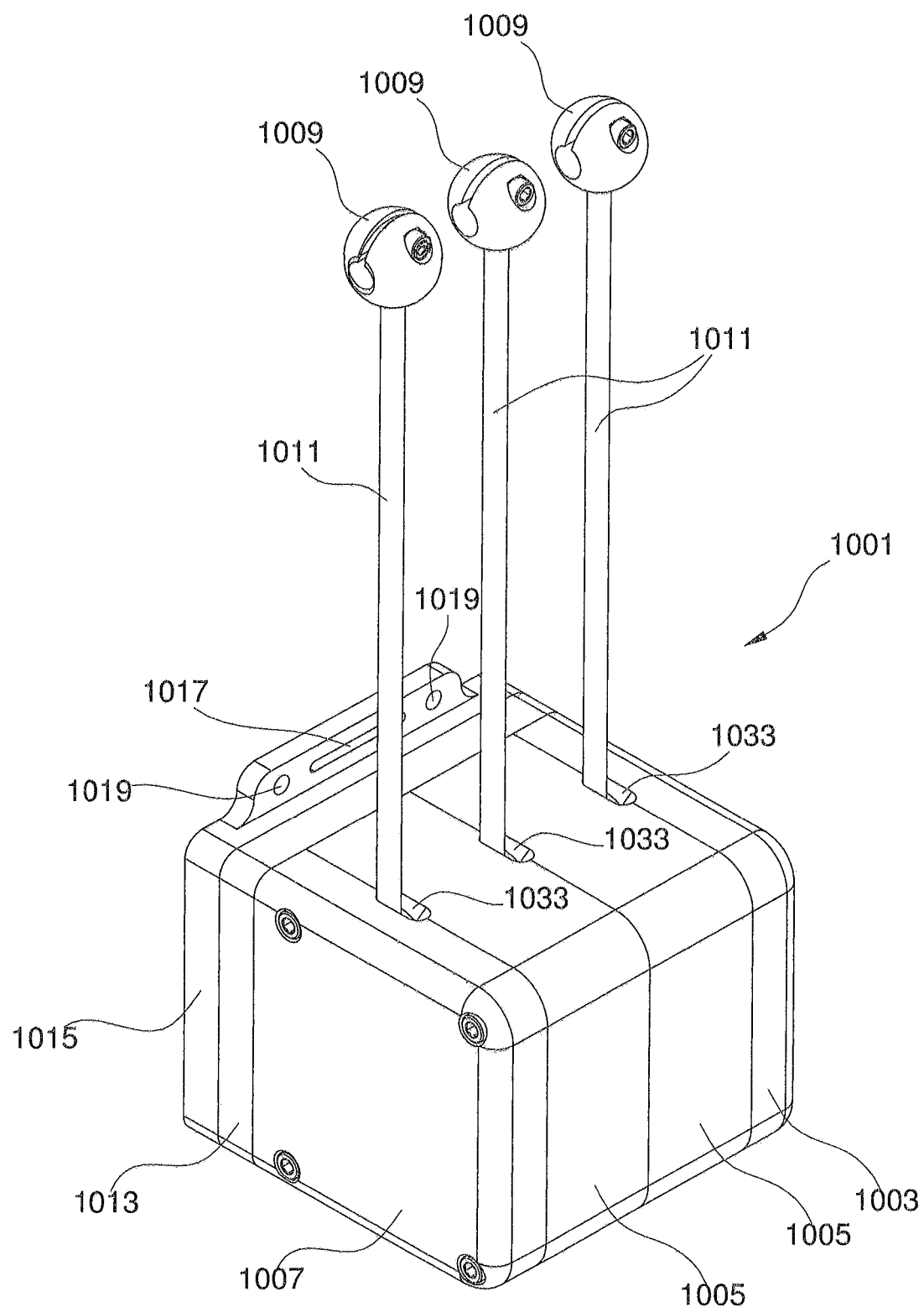
FIG. 10 is a perspective view of an alternate embodiment of a cable organization system according to the present application.

Referring now also to FIG. 10 in the drawings, an alternative embodiment of a modular cable organization system 1001 is shown. As opposed to cable organization system 100, which utilizes multiple independent cable management modules on a shared mounting plate, cable organization system 1001 utilizes multiple cable retraction systems held within one modular housing. Preferably, the multiple retraction systems are held between middle housings 1005, an end housing 1003 and an end cap 1007. Each middle housing 1005, as well as end housing 1003, supports a retraction system similar to that used in cable management modules 101 and 501.

Figure 11:
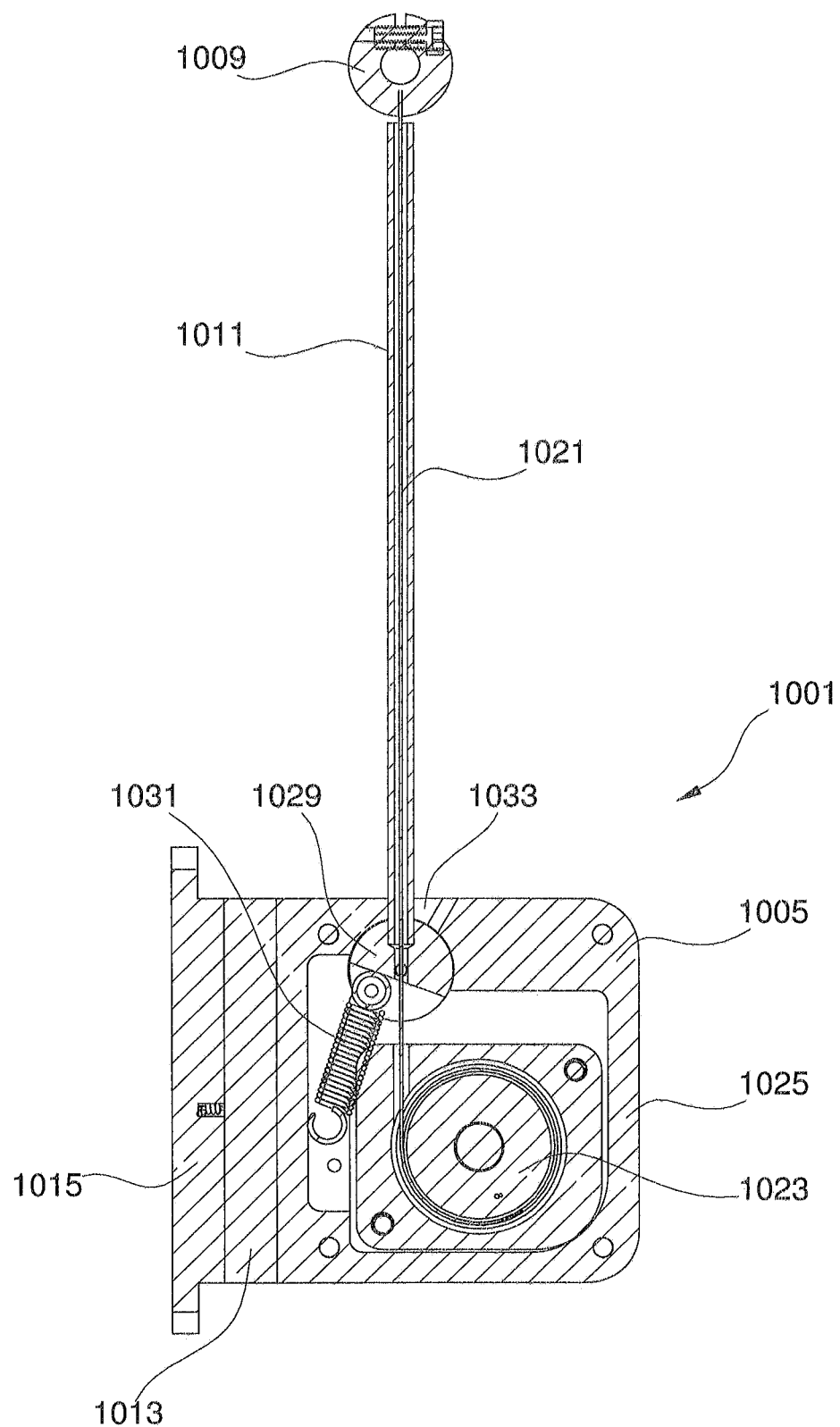
FIG. 11 is a cross-sectional view of the cable organization system of FIG. 10 taken along a vertical plane.

Referring now also to FIG. 11 in the drawings, each retraction system feeds a retractor cable 1021 through a guide tube 1011 to a cable clamp 1009. Retractor cable 1021, guide tube 1011, and cable clamp 1009 are substantially similar in form and function to retractor cable 125, guide tube 117, and cable clamp 113, respectively. Each retractor cable 1021 is stored on and wrapped around a spool 1023, which is supported by and held within retractor housing 1025, and winding tension is supplied to spool 1023 by a torsion spring (not shown). Spool 1023, retractor housing 1025, and the torsion spring (not shown) are substantially similar in form and function to spool 121, retractor housing 129, and torsion spring 127, respectively. The retraction components such as spools 1023 and 121, retractor cables 1021 and 125, and torsion springs 1027 and 127 may be commonly available components typically used in retracting systems, or may be specifically designed for cable organization systems 100, 501, 1001.

Each guide tube 1011 is mounted to a pivot 1029. Pivot 1029 is a single-axis pivot that moves a connected guide tube 1011 between a generally upright position and a tilted position. Tension is supplied to pivot 1029 by pivot spring 1031. As illustrated, pivot spring 1031 is a coil spring that pulls on pivot 1029. Pivot spring 1031 should be understood to include any effective spring for supplying a rotational force to pivot 1029, such as a torsion spring, wound spring, elastic strap, or other tension spring element. Alternative embodiments of cable organization systems which are primarily similar to system 1001 may utilize compression spring elements rather than tension spring elements to provide rotational force to pivot 1029. Each pivot 1029 preferably has a guide tube 1011 extending into pivot 1029, and each pivot 1029 preferably has an opening and a recessed portion sufficient for retractor cable 1021 to pass through pivot 1029 into guide tube 1011. Alternatively, guide tube 1011 may be mounted to one side of pivot 1029 such that no opening is necessary in pivot 1029.

Figure 12:
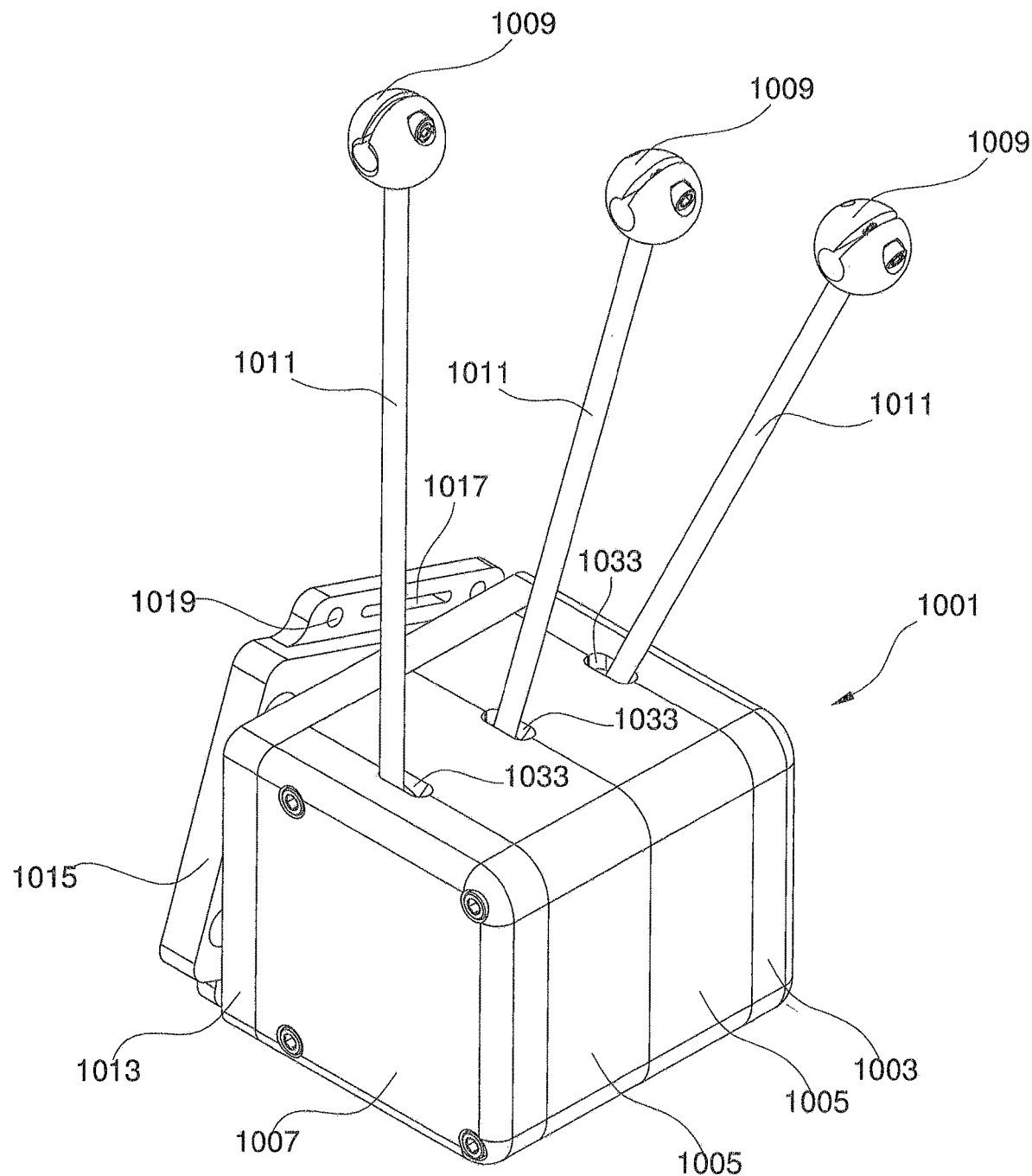
FIG. 12 is a perspective view of an alternate embodiment of a cable organization system according to the present application.

Referring now also to FIG. 12 in the drawings, the range of motion for each guide tube 1011 is limited by openings 1033 formed between middle housings 1005, or between a middle housing 1005 and an end housing 1003 or end cap 1007. Because each pivot 1029 is a single-axis pivot, cable organization system 1001 pivots in order to provide cable clamps 1009 with multiple-axis range of motion. Middle housings 1005, along with end housing 1003 and end cap 1007, are mounted to a backing plate 1013. Backing plate 1013 is rotatably coupled to a mounting plate 1015. Backing plate 1015 contains mounting apertures 1017 and 1019 such that cable organization system 1001 may be mounted to equipment, furniture, fixtures, or directly to walls with the use of straps, screws, bolts, or other mounting hardware. Alternatively, mounting plate 1015 may be configured to adhere to mounting surfaces.

Figure 13:
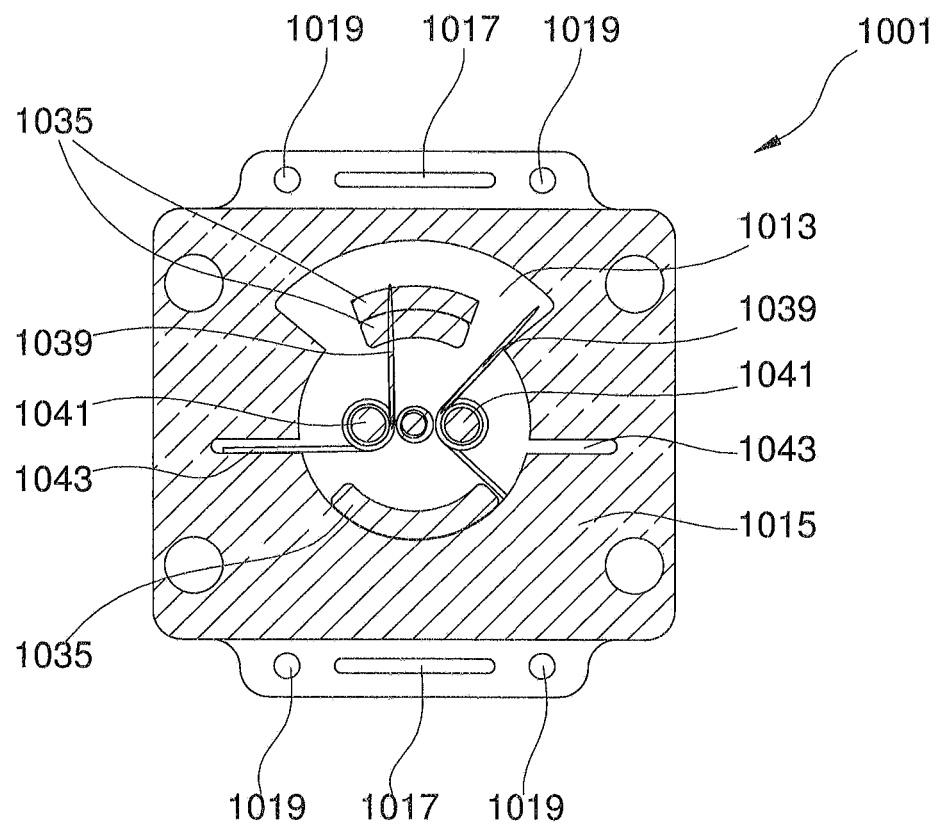
FIG. 13 is a rear cross-sectional view of the cable organization system of FIG. 12 taken along a vertical plane.

Referring now also to FIG. 13 in the drawings, the pivoting mechanism between backing plate 1013 and mounting plate 1015 is shown. Backing plate 1013 and mounting plate 1015 contain concentric interfacing rails 1035 that allow backing plate 1013 to rotate about pivot 1037 with respect to mounting plate 1015. Springs 1039 are held on posts 1041 on backing plate 1013 and in spring seats 1043 in mounting plate 1015. The range of motion for backing plate 1013 about pivot 1037 is limited by interference between springs 1039 and rails 1035. For clarity, guide tubes 1011 and cable clamps 1009 are not shown. Guide tubes 1011 and cable clamps 1009 though should be understood to extend upwards from cable organization system 1001 in FIG. 13.

Figure 14:
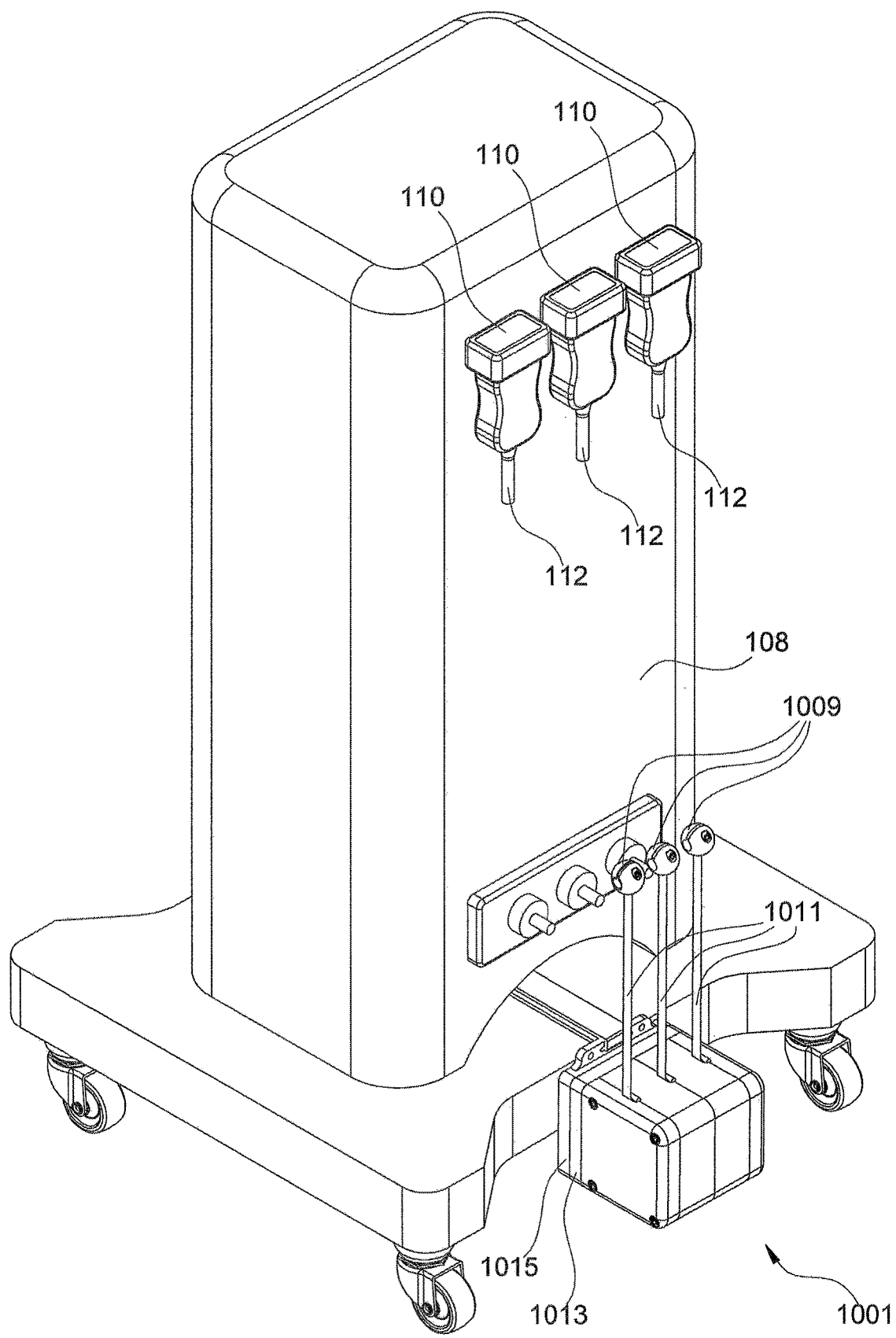
FIG. 14 is a perspective view of the cable organization system of FIG. 10 attached to an ultrasound machine.

Referring now also to FIG. 14 in the drawings, cable organization system 1001 is shown mounted to ultrasound machine 108, machine 108 having probes 110 connected to ultrasound machine 108 by cables 112. For clarity, portions of cables 112 of ultrasound machine 108 are not shown. The arrangement of cables 112 within cable clamps 1009 is substantially similar to the arrangement of cables 112 within cable clamps 113 as described above with regard to cable organization system 100. In effect, cable organization system 1001 provides the same or similar advantages and protections to ultrasound machine 108 that cable organization system 100 provides.

Figure 15:
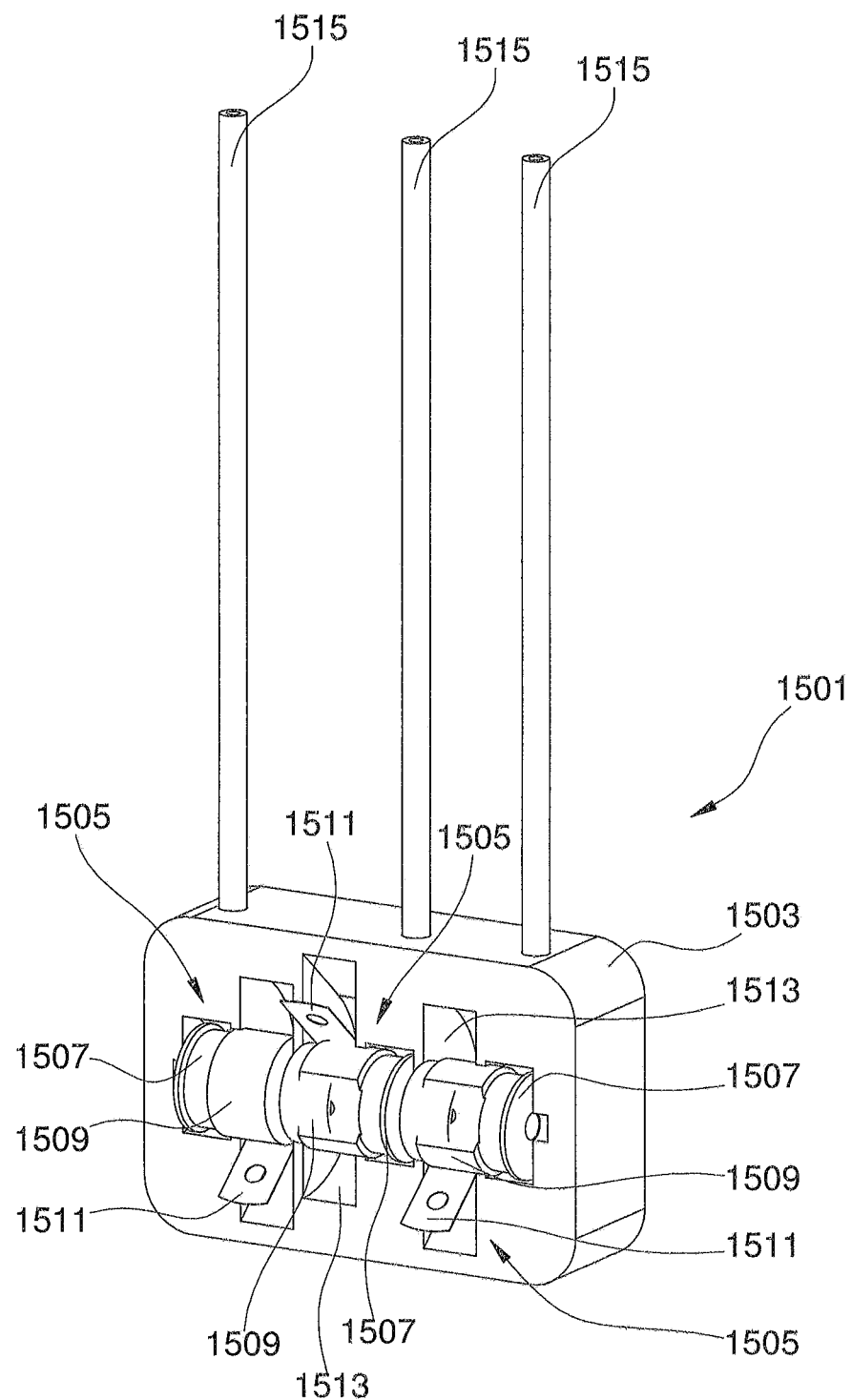
FIGS. 15 and 16 are perspective views of alternative embodiments of a retraction system according to the present application.

Referring now also to FIG. 15 in the drawings, a retraction system 1501 having fixed guide tubes is shown. Housing 1503 holds multiple operating cylinders 1505. Each operating cylinder 1505 has a spool segment 1507 and a tension segment 1509. Tension segments 1509 support wound springs 1511, which are seated into spring chambers 1513. A fixed guide tube 1515 is attached to housing 1503 with respect to each spool segment 1507. In use, a retractor cable is wound about spool segment 1507, and one end of the retractor cable is fed through an aperture in housing 1503 into and through a fixed guide tube 1515. A cable clamp such as cable clamp 113 is attached to the retractor cable and is supported at the end of a fixed guide tube 1515. Guide tube 1515 is preferably a rigid non-pivoting guide tube. Retracting tension is supplied to cable clamps from wound springs 1511. Guide tubes 1515 do not have pivoting mechanisms. As such, retractions system 1501 alone does not provide any pivoting motion to guide tubes 1515 and any cable clamps.

Figure 16:
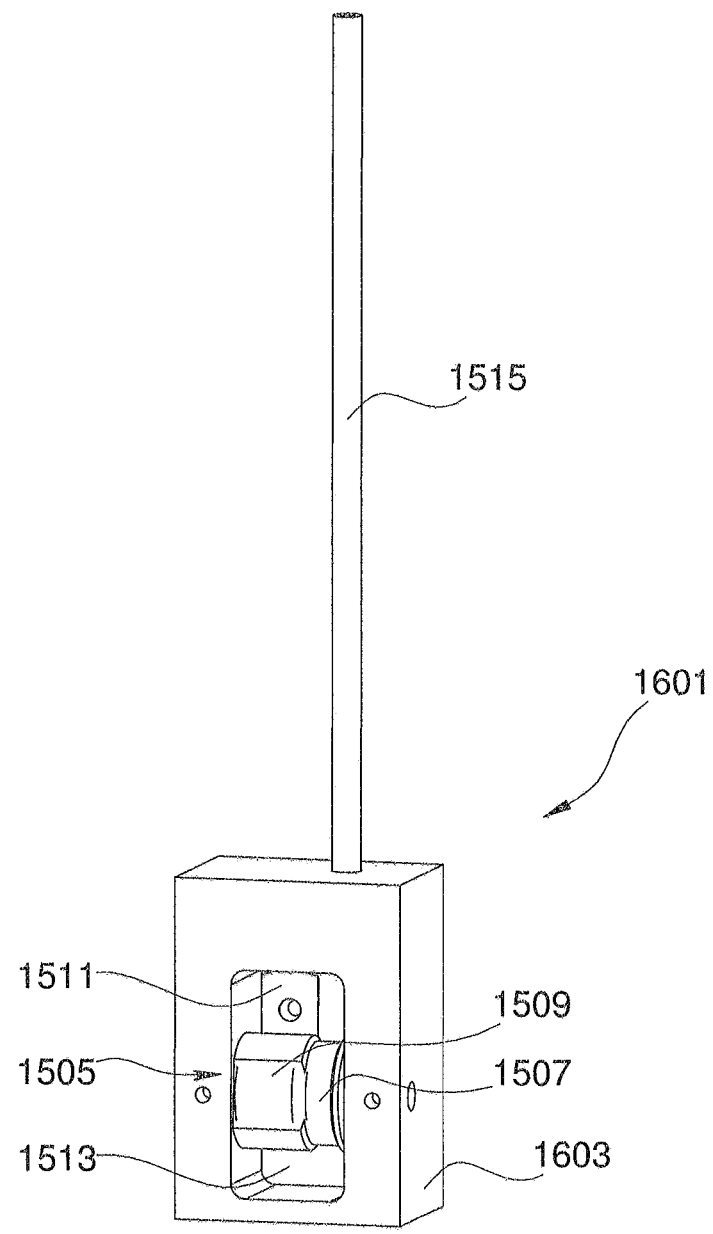

Referring now also to FIG. 16 in the drawings, a retraction system 1601 having a fixed guide tube is shown. Retraction system functions in an identical or substantially similar manner to retraction system 1501. However, system 1601 has a housing 1603 that supports only one operating cylinder 1505 and one guide tube 1515. As in system 1501, guide tube 1515 in system 1601 is a rigid non-pivoting guide tube. Other embodiments of retraction systems 1501 and 1601, or any other cable management modules, may utilize flexible guide tubes, or guide tubes which combine flexible and rigid portions.

It is apparent that a system with significant advantages has been described and illustrated. The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description and claims. Although the present embodiments are shown above, they are not limited to just these embodiments, but are amenable to various changes and modifications without departing from the spirit thereof.

We claim:

1. A cable management module, comprising:
a housing;
a spool carried by the housing;
a spool tensioner operably associated with the spool;
a pivot member coupled to the housing, the pivot member being operable between a selected non-pivoted position and a pivoted position;
a guide tube having a first end and a second end, the first end being coupled to the pivot member;
a retractor cable wound about and dispensed from the spool, the retractor cable passing through the guide tube; and
a cable clamp coupled to the retractor cable and being biased against the second end of the guide tube by the spool tensioner.

2. The cable management module according to claim 1, further comprising:
a pivot tensioner coupled to the pivot member for biasing the pivot member in the selected non-pivot position.

3. The cable management module according to claim 1, further comprising:
a guide tube opening formed in the housing for limiting the range of motion of the guide tube.

4. The cable management module according to claim 3, wherein the pivot member is a single-axis pivot, such that the guide tube pivots about a single axis.

5. The cable management module according to claim 3, wherein the pivot member is a multi-axis pivot, such that the guide tube pivots about multiple axes.

6. The cable management module according to claim 1, wherein the pivot member is a coiled spring through which the guide tube extends, such that the coiled spring acts as a multi-axis pivot, thereby allowing the guide tube to pivots about multiple axes.

7. The cable management module according to claim 1, wherein the cable clamp is configured to releasably couple an equipment cable to the retractor cable.

8. A cable organization system, comprising:
a mounting plate configured for attachment to a structure; and
at least one cable management module, each cable management module comprising:
a housing;
a spool carried by the housing;
a spool tensioner operably associated with the spool;
a pivot member coupled to the housing, the pivot member being operable between a selected non-pivoted position and a pivoted position;
a guide tube having a first end and a second end, the first end being coupled to the pivot member;
a retractor cable wound about and dispensed from the spool, the retractor cable passing through the guide tube; and
a cable clamp coupled to the retractor cable and being biased against the second end of the guide tube by the spool tensioner.

9. The cable organization system according to claim 8, further comprising:
mounting apertures in the mounting plate; and
mounting straps configured to extend through the mounting apertures, so as to secure the mounting plate to the structure.

10. The cable organization system according to claim 9, wherein the mounting plate is configured to support a plurality of cable management modules.

11. The cable organization system according to claim 9, further comprising:
a backing plate disposed between the mounting plate and the at least one cable management module, the backing plate being attached to the mounting plate and being configured to support the at least one cable management module.

12. The cable organization system according to claim 11, wherein the backing plate is rotatably coupled to the mounting plate about an axis perpendicular to the backing plate.

13. The cable organization system according to claim 12, wherein the backing plate is biased in a selected position relative to the mounting plate.

14. A cable organization system, comprising:
a mounting plate for mounting the cable organization system to a structure; and
a cable management assembly coupled to the mounting plate, the cable management assembly comprising:
a modular housing; and
a plurality of retraction systems disposed within the modular housing, each retraction system comprising:
a spool coupled to the modular housing;
a spool tensioner operably associated with the spool;
a pivot member coupled to the modular housing, the pivot member being operable between a selected non-pivoted position and a pivoted position;
a guide tube having a first end and a second end, the first end being coupled to the pivot member;
a retractor cable wound about and dispensed from the spool, the retractor cable passing through the guide tube; and
a cable clamp coupled to the retractor cable and being biased against the second end of the guide tube by the spool tensioner.

15. The cable organization system according to claim 14, wherein the cable clamp is configured to releasably couple an equipment cable to the retractor cable.

16. The cable organization system according to claim 14, wherein the modular housing comprises:

a slot for receiving each guide tube, each slot being configured to selectively restrict the range of motion of each guide tube.

17. The cable organization system according to claim 14, further comprising:
a backing plate disposed between the mounting plate and the cable management assembly, the backing plate being rotatably coupled to the mounting plate and the cable management assembly being fixedly coupled to the backing plate.

18. The cable organization system according to claim 17, wherein the backing plate is spring biased in a selected position relative to the mounting plate.

19. The cable organization system according to claim 14, wherein each pivot member operates independently, such that each guide tube pivots relative to the modular housing between a generally upright position and a pivoted position.

20. The cable organization system according to claim 14, further comprising:
one or more mounting members for securing the mounting plate to the structure.

* * * * *